US010405782B2

(12) United States Patent
Pologe et al.

(10) Patent No.: US 10,405,782 B2
(45) Date of Patent: Sep. 10, 2019

(54) PHOTOPLETHYSMOGRAPHIC DEVICE WITH MECHANICALLY-PROTECTED SENSOR CONNECTOR

(71) Applicants: Jonas Alexander Pologe, Boulder, CO (US); Theodore Philip Delianides, Boulder, CO (US)

(72) Inventors: Jonas Alexander Pologe, Boulder, CO (US); Theodore Philip Delianides, Boulder, CO (US)

(73) Assignee: Kestrel Labs, Inc., Boulder, CO (US)

( * ) Notice: Subject to any disclaimer, the term of this patent is extended or adjusted under 35 U.S.C. 154(b) by 582 days.

(21) Appl. No.: 15/296,466

(22) Filed: Oct. 18, 2016

(65) Prior Publication Data

US 2018/0103877 A1    Apr. 19, 2018

(51) Int. Cl.
*A61B 5/1455* (2006.01)
*A61B 5/0205* (2006.01)

(52) U.S. Cl.
CPC .......... *A61B 5/1455* (2013.01); *A61B 5/0205* (2013.01); *A61B 2562/0238* (2013.01); *A61B 2562/12* (2013.01); *A61B 2562/185* (2013.01); *A61B 2562/223* (2013.01); *A61B 2562/228* (2013.01)

(58) Field of Classification Search
CPC .............. A61B 5/1455; A61B 5/14551; A61B 5/14552; A61B 5/059; A61B 5/0205; A61B 2562/0233; A61B 2562/228; G02B 6/36; G02B 6/3624; G02B 6/3817; G02B 6/3825; G02B 6/3849
See application file for complete search history.

(56) References Cited

U.S. PATENT DOCUMENTS

| 4,738,506 | A | * | 4/1988 | Abendschein | ....... G02B 6/3849 385/19 |
| 5,509,096 | A | * | 4/1996 | Easley | ................ G02B 6/4298 385/19 |
| 5,533,615 | A | | 9/1996 | Carim et al. | |
| 5,786,592 | A | | 7/1998 | Hok | |
| 5,956,444 | A | * | 9/1999 | Duda | ................... G02B 6/3849 385/53 |
| 6,560,470 | B1 | | 5/2003 | Pologe | |
| 6,615,064 | B1 | | 9/2003 | Aldrich | |
| 6,647,279 | B2 | | 11/2003 | Pologe | |
| 7,313,424 | B2 | * | 12/2007 | Mayevsky | ........... A61B 5/0059 600/310 |
| 7,883,276 | B2 | * | 2/2011 | Davidson | ............. G02B 6/3849 385/53 |
| 2006/0153504 | A1 | * | 7/2006 | Suzuki | ................ G02B 6/3849 385/75 |
| 2008/0045822 | A1 | * | 2/2008 | Phillips | .............. A61B 5/14553 600/323 |
| 2008/0106792 | A1 | * | 5/2008 | Lash | .................. A61B 5/14552 359/618 |
| 2015/0078710 | A1 | * | 3/2015 | Sato | ..................... G02B 6/3849 385/78 |

* cited by examiner

Primary Examiner — Eric F Winakur

(57) ABSTRACT

A photoplethysmographic device including at least one laser light source and further including a protective sensor connector that has a protective flap (350), a mechanism (340) for controlling movement of the protective flap, and a plurality of interconnections, at least one of which is an optical connection (240). The movement of the protective flap designed to provide at least a substantially open position and a substantially closed position.

18 Claims, 7 Drawing Sheets

PHOTOPLETHYSMOGRAPHIC DEVICE WITH MECHANICALLY-PROTECTED SENSOR CONNECTOR

STATEMENT REGARDING FEDERALLY SPONSORED RESEARCH OR DEVELOPMENT

This invention was made with government support under R44 HL073518 awarded by the National Institutes of Health. The government has certain rights in the invention.

BACKGROUND—PRIOR ART

U.S. Patents

| Pat. No. | Kind Code | Issue Date | Patentee |
| --- | --- | --- | --- |
| 5,533,615 | | Sep. 10, 1996 | Carim et al. |
| 5,786,592 | | Jul. 28, 1998 | Hok |
| 6,560,470 | B1 | May 6, 2003 | Pologe |
| 6,615,064 | B1 | Sep. 2, 2003 | Aldrich |
| 6,647,279 | B2 | Nov. 11, 2003 | Pologe |

BACKGROUND OF THE INVENTION

In the science of photoplethysmography, light is used to illuminate or trans-illuminate living tissue for the purpose of providing noninvasive measurements of blood analytes, hemodynamic parameters, or tissue properties. In this monitoring modality light is directed into living tissue (the "tissue-under-test") and a portion of the light that is not absorbed by the tissues, or scattered in some other direction, is detected a short distance from the point at which the light entered the tissue. The detected photoplethysmographic signal (the pulsatile optical signal exiting the living tissue) is converted into an electronic signal that is used to calculate blood analyte levels such as arterial blood oxygen saturation, total hemoglobin concentration, blood glucose levels, serum bilirubin levels, and/or hemodynamic parameters such as heart rate, cardiac output, blood oxygen content, or tissue perfusion. A device which detects and processes photoplethysmographic signals to measure the levels of various blood analytes and/or various hemodynamic parameters is referred to as a photoplethysmographic measurement apparatus, photoplethysmographic device, photoplethysmographic monitor, or photoplethysmographic instrument. The first widespread commercially-used photoplethysmographic device in medicine was the pulse oximeter, a photoplethysmographic device designed to measure arterial blood oxygen saturation.

In the typical configuration seen in pulse oximeters, a unit or electronics module called the "monitor" contains various circuitry for controlling light emitters, electronics for receiving and processing signals from a detector located on the tissue-under-test, a user interface for controlling the device, and a visual display from which the user can observe measurement results in real time or as trend data. The monitor, or electronics module, is connected to a sensor via a cable called the "patient cable" or the "sensor cable". The light emitters, or light sources, can be located either within the electronics module or in the sensor that, in use, is placed on the tissue-under-test.

The sensor arrangement most commonly seen in photoplethysmography over the last 30 years has been a fingertip sensor that positions light emitting diodes (LEDs) and a photodetector on opposite sides of the tissue-under-test. This arrangement was predated, however, by an oximeter from the 1970s, the Hewlett-Packard 47201A Ear Oximeter, which was not a photoplethysmographic device and the Minolta-Marquest SM-32 Oxygen Saturation Monitor which was a photoplethysmographic device. In both of these devices, a tungsten light source and fiber optic bundles were used for delivery of light to and from the tissue-under-test. The advent of inexpensive and efficient LEDs in the 1980s resulted in a more effective device that allowed efficient light delivery to the tissue, and this has become the preferred arrangement in present-day pulse oximeters. In certain circumstances, for example oximetry sensors used in the high magnetic field environment of MRI (Magnetic Resonance Imaging) devices, there has still been a need for fiber optic delivery of the light to and from the tissue. In such cases, the LEDs may be located within the photoplethysmographic monitor box and their light is directed into one or more fiber optic light guides (or lightguides). The light guides are routed from the LEDs within the monitor box to a connector, normally located on the monitor front panel and sometimes called a monitor sensor connector. The light can then travel through a mating connector (also called the proximal connector or the patient connector) of the patient cable out to the patient sensor, where the light is then emitted into the tissue-under-test.

A more recent improvement to the field of photoplethysmography has been the introduction of laser light sources. The introduction of lasers to pulse oximetry provides the opportunity to expand the measurement capabilities of photoplethysmography from the measurement of one blood analyte, specifically oxygen saturation, to the measurement of multiple blood analytes and physiological parameters. The narrow spectral bandwidth of laser light improves the resolution, accuracy, and precision of photoplethysmographic measurements, thus making technically feasible the accurate measurement of analytes such as oxyhemoglobin, carboxyhemoglobin, methemoglobin, reduced hemoglobin, and a number of other analytes. Despite years of work in the field, however, there is still no commercially-available laser-based device that accurately makes photoplethysmographic measurements of these additional parameters.

Not unexpectedly, the use of lasers in photoplethysmography introduces a number of new problems in the design and implementation of commercially-viable photoplethysmographic devices. Among these is that it is technically very difficult to position laser light sources in a sensor intended to be placed directly on the tissue-under-test, particularly when multiple light sources are required. One solution is to position the laser light sources in the main monitor box, or in a small enclosure at a position intermediate to the monitor box and the sensor, and deliver the light out through the monitor sensor connector, through a patient cable to the sensor, and finally into the tissue-under-test using one or more optical light guides. These light guides may be any one of a number of optical elements, or a chain of optical elements, including glass or plastic optical fibers, liquid-filled tubes, fiber optic bundles, or other configurations of light pipes. The photoplethysmographic signal returning from the tissue-under-test can be in the form of optical signals, i.e. returning to the monitor via another light guide, or set of light guides, or as an electronic signal generated by a photodetector located in proximity to the tissue-under-test. Such a system requires cabling and connectors for both electrical and optical signals.

While a photoplethysmographic monitor utilizing a combination of electrical conductors and light guides for transmitting electrical and optical signals to and from the sensor could have separate patient cables—for example, one for electrical signals and a second for optical signals—these two types of signals can also be transmitted in a combined manner in a single hybrid electro-optical cable. Note also that the patient cable, or the sensor cable as it is sometimes called, can in actuality be a series of interconnected cables and connectors shuttling signals between the photoplethysmographic monitor and the patient sensor.

Fiber optic light delivery is the preferred method to deliver light in an instrument where the photoplethysmographic light sources are lasers, but the use of optical light guides in general, and optical fibers specifically, introduces additional challenges to the design of a commercially-viable instrument. The typical pulse oximeter uses sensors and patient cables that are replaced frequently due to normal wear and tear. In the case of single-patient-use sensors (also referred to as disposable sensors) the sensors are replaced after use on every patient. Thus the monitor's "sensor connector," a connector typically located on the monitor front panel, experiences a great many insertion and removal cycles over its lifetime. Whereas electrical interconnections might be capable of withstanding repeated connections and disconnections, the same is not always true for optical interconnections, as they are susceptible to considerable loss of transmission efficiency due to contamination with dirt, dust, moisture, and oils at the optical interface. Therefore, unlike optical interconnections used in fiber-based telecommunications systems where plugging and unplugging might occur only a few times over the lifetime of the connectors, a patient cable connector (the proximal connector to the patient sensor) in a photoplethysmographic system may be connected and disconnected multiple times each day.

Furthermore, the connector (including any optical interconnections) of a photoplethysmographic system might be manipulated by personnel who are unskilled in the proper handling of optical connectors and components. When left in an unconnected state, the optical surfaces might be exposed to the environment for many days or months. An exposed monitor sensor connector would leave the optical surface ends of any light guides in the connector susceptible to damage from fingertips, tools, or other foreign objects touching the exposed ends, or susceptible to dust, dirt, moisture, oils, and other contaminants settling on, or being brought into contact with, the exposed ends. This would result in the need for frequent cleaning to avoid degradation in light transmission through the cable system. Such contamination might also shorten the optical connector lifetime. The issue of contaminants affecting light transmission efficiency is particularly exacerbated with the use of small-diameter optical fibers, which, although permitting the creation of highly-flexible cabling systems, are susceptible to light blockage from miniscule dirt and dust particles that can easily be larger than the light transmission core of the fiber.

The Minolta/Marquest Model SM-32 Oxygen Saturation Monitor was perhaps the first pulse oximeter put into clinical use, predating now omnipresent conventional "LED-based" pulse oximeters. It used a broadband tungsten light bulb, a series of optical filters, and two fiber optic bundles to deliver light to, and receive light from, the tissue-under-test. Given the inefficiencies in coupling light from a diffuse tungsten source to small-diameter fiber optics, the Minolta/Marquest device required thick fiber bundles that were approximately 2.5 mm diameter and were made up of numerous individual fiber light guides. The patient cable connector and the monitor box sensor connector mated at the front panel, i.e. the bulkhead, where the two pairs of fiber bundles were each coaxially aligned. In the Minolta/Marquest device this front panel connector was a large screw-together device designed to be left in place over the long term, thus protecting the fiber ends from damage. Accordingly, the fiber optic bundles on both the cable and monitor side lacked any protection on their end faces. Furthermore, due to the large diameter of the fiber bundle in this monitor, small particles of dirt, dust, moisture, or oils had relatively little impact on the total light transmission. While this design was functional, it was certainly not optimal.

A similar arrangement was used in the Hewlett-Packard 47201A Ear Oximeter, where a bulky set of light guides was used to deliver light to and from the tissue-under-test, in this case the pinna of the ear. As with the Minolta/Marquest device, the cable was not meant to be detached from the main monitor often, and the large light guide diameter helped make it less susceptible to loss of transmission from contaminants on the optical surfaces.

Current pulse oximetry patient cables are often semi-disposable and must withstand multiple connections and disconnections each day. Also, in an effort to minimize the effects of patient motion on the photoplethysmographic signal, the mass of the patient cables is typically kept to a minimum. Furthermore, a heavy optical cable can easily pull a sensor from the tissue-under-test. Large fiber bundles are thus not viable for most modern commercial photoplethysmographic uses. But, as mentioned earlier, the smaller the light guide, the more sensitive its performance is to contaminations that might block light transmission.

The light guides used with laser light sources in a laser-based oximeter can be smaller in diameter than a human hair in part because the laser light sources (such as semiconductor diode lasers) are physically very small and the light that they emit is fairly directional, making them easier to couple into small diameter fibers than LED light sources. But while the smaller fibers provide the benefits of reducing cable diameter and increasing flexibility, the potential problems associated with unprotected optical connectors, particularly on the monitor side where the connector might be expected to last the lifetime of the monitor, is only growing with each new generation of photoplethysmographic monitor that uses ever-smaller light guides to deliver light to the patient sensor.

It is the problem of protecting the optical light guides from damage or contamination that might affect the transmission of light to the tissue-under-test, and the maintaining of low-loss transmission through the connector interface, that the current invention is intended to address.

U.S. Pat. No. 6,560,470 shows a laser-based photoplethysmographic device with electrical lockout to shut off the laser light sources when the mating patient cable is disconnected from the device. This design protects the user from exposure to stray light emissions emitted from the monitor front panel, but it does not protect exposed fiber optic ends from damage or contamination. A commercial device was never developed out of this work, and the inventor never recognized the need to address the problems that might arise if exposed fiber optic ends come in contact with dirt, dust, moisture, oils, tools, fingertips, or other foreign objects. Thus, the invention does not teach how to protect and maintain the optical connections in the front panel connector.

U.S. Pat. No. 5,786,592 reveals a fiber-optic based pulse oximeter for use in MRI environments. Fiber optic bundles are used to deliver light to the tissue-under-test and to return photoplethysmographic signals back to a photodetector located inside the monitor box. This patent shows a continuous optical path from the LED emitters through one fiber bundle to the tissue-under-test. Similarly, it shows a single continuous light path through a second fiber bundle from the tissue-under-test back to the detector. There is no need to provide a means to protect the ends of the light guides at the front panel connector because no such connector is disclosed. The inventor also does not discuss problems that might arise if contaminants or foreign objects come in contact with the end faces of the fiber optic bundles used in the device and thus does not offer or suggest a solution.

U.S. Pat. No. 5,553,615 reveals a photoplethysmographic device for the noninvasive prediction of hematocrit. This patent employs a "mechanical shutter 324". Its purpose and function is "to vary the light intensity interrogating the mammalian tissue (e.g., a finger) without altering the relative spectral intensity of the light." It is designed as an adjustable attenuator to control the overall light intensity that reaches the tissue, so as to eliminate the need to adjust the electrical current driving the broadband incandescent emitter, which could alter its spectral (i.e. power vs. wavelength) content and affect measurement accuracy. The shutter of the patent is buried within the device and is not present at the front panel bulkhead sensor connector, thus it does not protect the fiber optic ends at a sensor connector from damage due to dirt, dust, moisture, oils, tools, fingertips, or other foreign objects, nor is this potential problem discussed. In fact, as with U.S. Pat. No. 5,786,592, this patent does not reveal a sensor connector or front panel connector whatsoever. The drawings show only a single continuous light guide from the optical source to the finger and a second set of continuous light guides from the tissue-under-test to the receiving optics for the photodetectors. Furthermore, the device uses a fiber optic bundle, as opposed to a single, small-core optical fiber, and is thus less sensitive to optical losses due to contamination of or damage to any optical light guide end faces. In the apparatus revealed in this patent, there are no ends of light guides in need of protection and therefore no such protective mechanism is discussed or revealed.

U.S. Pat. No. 6,615,064 is a blood component analyzer that uses photoplethysmographic and other signals generated at a finger sensing site. This patent includes one embodiment where "two or more light sources are alternately switched on or with their emissions alternately blocked using electromechanical shutters (e.g., Melles-Griot electronic shutter)." In another embodiment where "the light source 122 is preferably a heater coil" and "there is a risk of thermal injury from excessive exposure to heat or infrared energy . . . an electromechanical shutter 152 (e g. Malles-Griot [sic] electronic shutter) is interposed between the light source 22 and the digit 14." In both embodiments of this patent, the shutter is used to create alternating periods of "dark" and "light" optical output in a manner similar to the chopper wheel in U.S. Pat. No. 5,553,615. In neither case, however, does this shutter provide a protective function for a light guide at a cable connection. The inventor also does not discuss the problems of dirt, dust, oils, and moisture contaminating the end faces of the fibers or fingertips, tools, or other foreign objects damaging delicate optical surfaces, nor does he show an apparatus that would mitigate these problems.

U.S. Pat. No. 6,647,279 discusses light source emitter that might be located either in the main monitor or in the cable or sensor. The inventor does not discuss details on the connector arrangement between the main monitor and the patient cable, nor does he address the issues of protecting the fiber optic ends at a connector-to-cable interface from contamination or damage.

Because small diameter fiber optic light guides are the preferred method for delivering the illuminating light to the tissue-under-test in a modern photoplethysmographic device when lasers are the chosen light source, there are more stringent requirements for the interconnections between the monitor and the sensor cabling than those seen in conventional pulse oximetry systems. Among these is the need for a sensor connector on the monitor that protects the fiber optic interconnections from light blockage or damage due to exposure to dirt, dust, moisture, and oils; protects the optical surfaces from unintended contact with fingertips, tools, or other objects; and maintains a clean mating surface for the optical interconnections.

SUMMARY OF THE INVENTION

In accordance with one embodiment a photoplethysmographic device with protective sensor connector comprises a monitor, patient cable, and sensor arranged such that the monitor's protective sensor connector includes a protective flap, with movement controlled by an included mechanism, that can be positioned over the sensor connector interconnections and, more specifically, the optical interconnections, whenever the patient cable is detached from the monitor. This advantage contributes to the creation of a useful device for accurate, high-resolution photoplethysmographic measurements. This and other advantages will become apparent from review of the following description and the accompanying drawings.

DETAILED DESCRIPTION OF THE INVENTION

Figure 1:
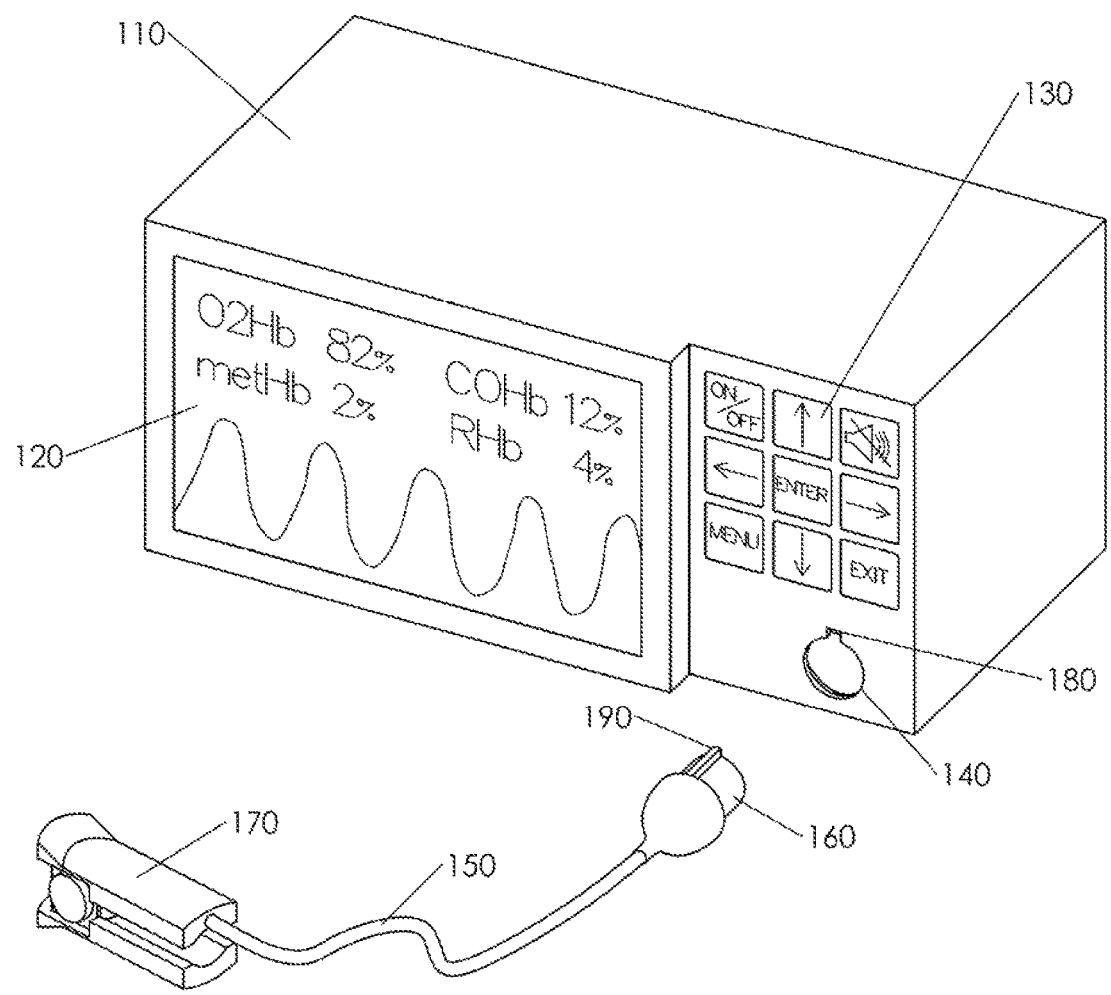
FIG. 1: Photoplethysmographic device with protective sensor connector.

One embodiment of a photoplethysmographic device with protective sensor connector is shown in FIG. 1. It includes a monitor or electronics module 110 that processes photoplethysmographic signals. Typically that electronics module also includes a visual display 120 which presents or outputs information such as measured values for the blood analyte levels or other physiological parameters, waveforms, alarms, and device status information to the clinician or end user of the monitor. The monitor 110 also typically includes a user control panel 130 for controlling the operation of the device. The electronics module 110 includes a sensor connector 140 that provides a point of connection for a patient cable 150 that has a patient cable connector 160, also known as a mating connector, connected to its proximal end and a patient sensor 170 connected to its distal end. The access hole of the sensor connector 140 has a uniquely-shaped keyway 180 that accepts a shape-matched engagement rib 190 that is part of the patient cable connector 160. The rib/keyway combination ensures that the patient cable connector 160 is properly aligned when inserted into the sensor connector 140, which ensures that the interconnections of the connector pair are properly mated. The engagement rib of the cable connector also provides a structural feature to engage and activate the mechanism of the protective sensor connector.

It should be noted that the electronics module 110 may be distributed into several different housings rather than constructed as a single unit as shown in FIG. 1. For example, display 120 or the user control panel 130 may be housed separately from other portions of the electronics module as they often are in multi-function or integrated monitoring systems such as are commonly found in operating rooms where the display electronics, for example, might be separated from the rest of the electronics module.

Furthermore, the sensor connector 140 shown in FIG. 1 is located on the front panel of the monitor 110, but it could also be positioned on the back, side, top, or bottom of, or other location within, the monitor. Furthermore, the sensor connector 140 could be located on a panel of a multi-parameter patient monitor, as part of a detachable or removable module some distance from the monitor, or even as part of a handheld photoplethysmographic system.

Figure 2:
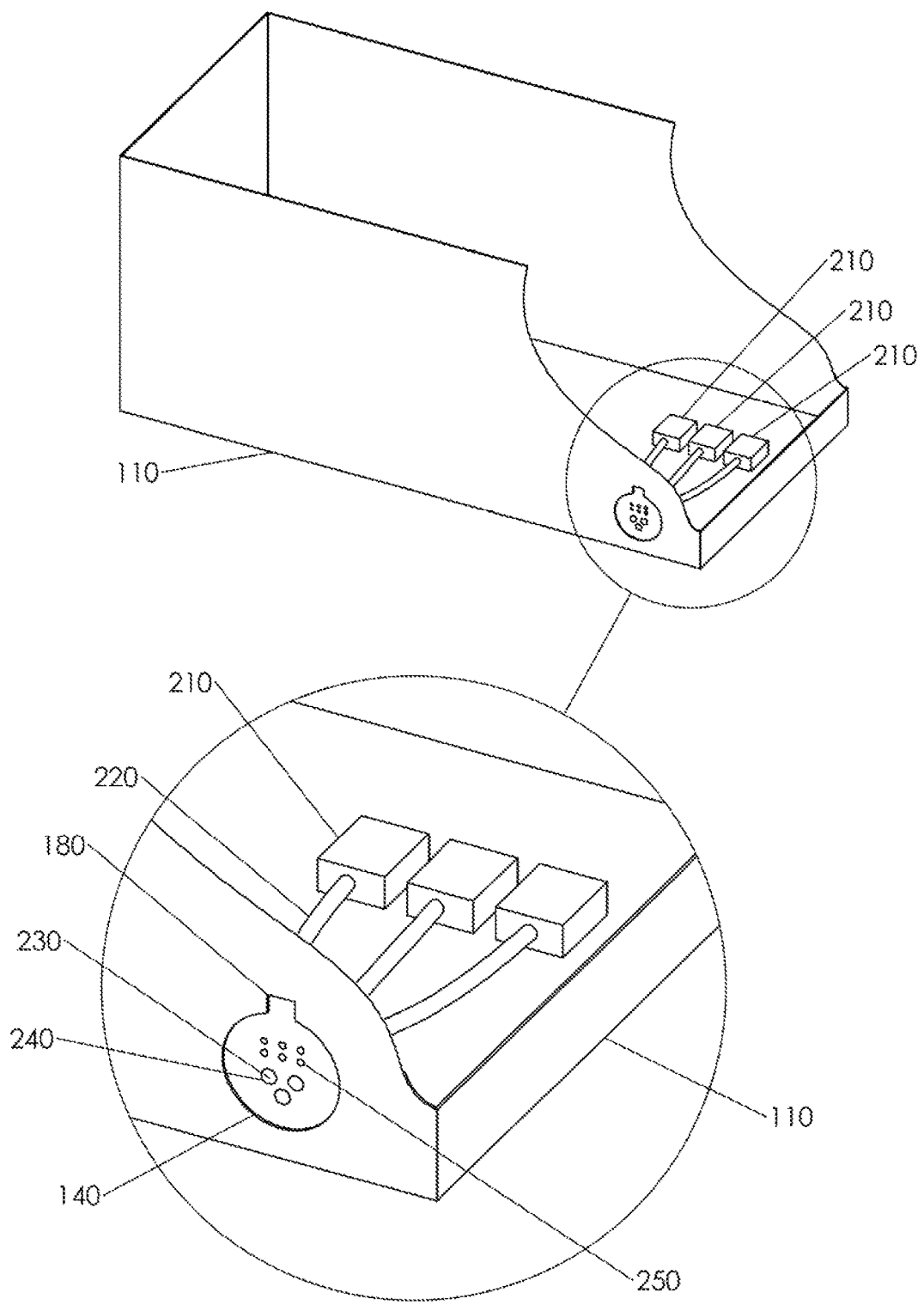
FIG. 2: Light sources and optical light guides with end faces in sensor connector.

A variety of light sources can be used in photoplethysmography, including light-emitting diodes (LEDs) located within the patient sensor 170 or, as in the case shown in FIG. 2, inside the electronics module 110 or within a sub-module or subassembly of the main electronics module. FIG. 2 shows three light sources 210, at least one of which is a laser. Each light source is coupled to a light guide (or lightguide) 220, such as an optical fiber that has a core and cladding with different refractive indices to facilitate low-loss propagation of light along the light guide. In the preferred embodiment of this laser-based photoplethysmographic device the core and cladding diameters of the optical fibers that are used are typically smaller than 300 um. The coupling of the light source or laser might be accomplished with various intervening optical components, however the end result is the launching of light from light source(s) 210 into the optical light guide(s) 220. The end of the light guide 220 terminates in an end face 230 that is an optical connection 240 disposed within the sensor connector 140. This end face 230 could be a simple, flat, 90° polished end or might be polished at a different angle, such as 8°, or have a lensed surface or the addition of other optical components or optical coatings, all with the end goal of creating a low-loss optical coupling when the patient cable connector 160 is mated to the sensor connector 140 of the electronics module. Similarly, the end face 230 of the light guide 220 could be supported in a ferrule or other carrier, but the end goal is to create a terminating optical connection 240 within the sensor connector 140. In FIG. 2 the light guides 220 from the three light sources 210 terminate in end faces that create three optical connections 240 within the sensor connector 140, which would mate with three corresponding optical connections in the patient cable connector 160 that are part of the light guides within the patient cable 150. In this example, the sensor connector also has six electrical connections 250, which could be metallic pins or receptacles of the type commonly seen in electronic connectors, and each electrical connection 250 is connected to electronics located within the electronics module 110. These electrical connections 250 mate with corresponding electrical connections in the patient cable connector that are electrically connected to conductors within the patient cable 150. Obviously there may be fewer or a greater number of electrical connections 250 or optical connections 240 in the sensor connector 140 of any given photoplethysmographic instrument depending on its specific design.

The sensor connector 140 in FIG. 1 is located in the lower right corner of the electronics module 110 of the photoplethysmographic system. It is shown isolated in cut-away views (with the front panel of the electronics module, and therefore also a portion of the sensor connector housing, removed) in FIGS. 3A and 3B. The sensor connector 140 is comprised of multiple interconnections, such as optical connection 240 and electrical connection 250, a protective flap 350, and a mechanism 340 in communication with the protective flap 350, all disposed within a housing 320. Because the mechanism is in communication with the protective flap 350, it can control its movement and position. One of these optical connections 240 includes the end face 230 of the optical light guide 220 coupled to light source or laser 210 previously shown in FIG. 2. The housing 320 is comprised of any structural elements within the electronics module 110 that are required to provide support structure for the interconnections, protective flap, and mechanism. The housing 320 might include separable components such as a connector body 330 mounted within a component of the electronics module, as shown in FIG. 3B, or it might be a single piece, or it would even be possible to dispose the protective flap, mechanism, and interconnections into a separate module connected some distance from the monitor, but the entire grouping of structural elements that support the protective flap, mechanism, and interconnections is the housing 320 of the sensor connector 140. The combination of the protective flap 350 and the mechanism 340 is also referred to as the shutter.

Figure 3A:
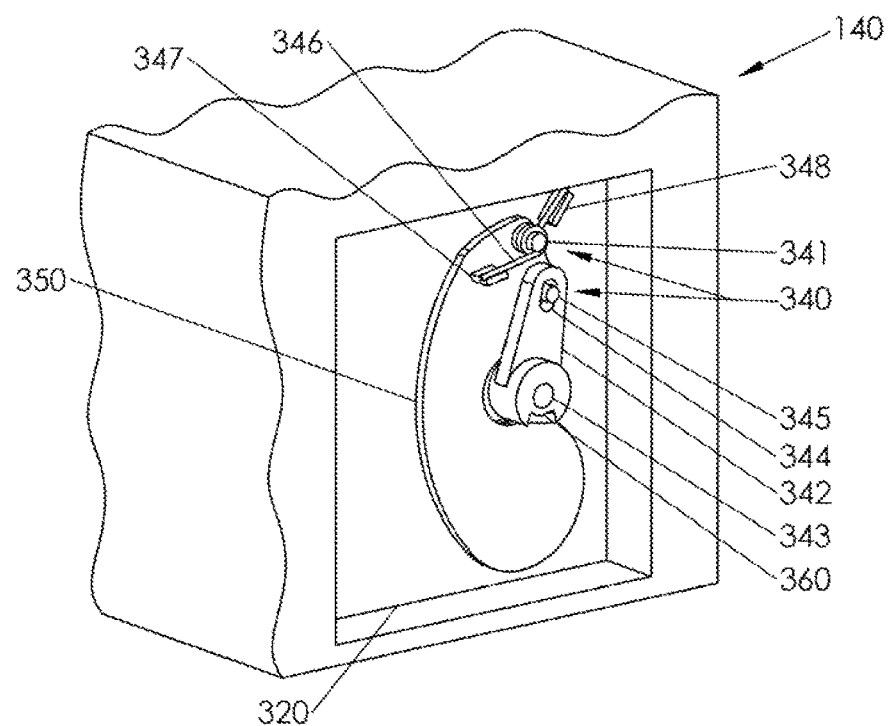
FIG. 3A: Cut-away view of sensor connector with protective flap in the closed position.
Figure 3B:
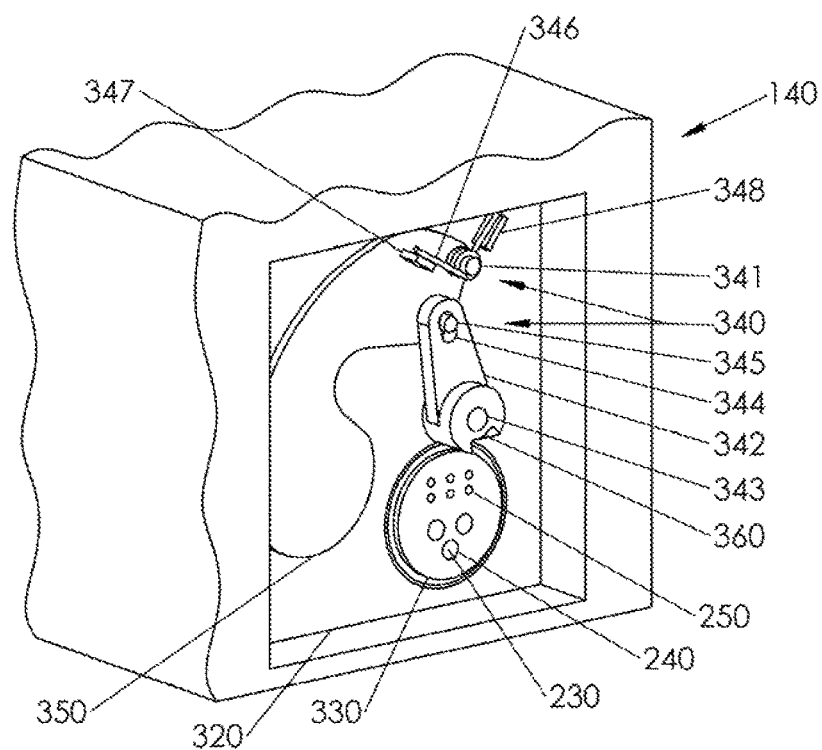
FIG. 3B: Cut-away view of sensor connector with protective flap in the open position.

As shown in the preferred embodiment shown in FIGS. 3A and 3B, the protective flap 350 and mechanism 340 are in communication so that the mechanism 340 can control movement of the protective flap 350, in this case the rotation of the protective flap 350 about flap pivot 341 attached to the housing 320. It should be noted that the mechanism 340 includes all of the pivots, levers, supports, stops, springs, slots, cams, and ribs and any other mechanical pieces that are necessary to operate the movement of the protective flap as explained in detail below. The mechanism includes a lever 342 that rotates about a lever pivot 343 and has a coupler slot 344 that rides on coupler pivot 345 that is part of the protective flap 350 and a torsion spring 346 mounted on flap pivot 341. Torsion Spring 346 has its legs constrained by a first spring stop 347 attached to the protective flap 350 and second spring stop 348 attached to housing 320. The lever 342 also has an engagement slot 360 that accepts the engagement rib 190 of the patient cable connector 160. The engagement slot of the lever has a helical-shaped side wall surface. Note that in this preferred embodiment the protective flap 350 has portions of the mechanism 340 built directly onto it, and thus this part serves two purposes, i.e. a flap portion that provides a protective cover for the sensor connector interconnections and additional structural elements, specifically the elongated linkage-like shape, the coupler pivot 345, and the spring stop 347, that are part of the mechanism 340.

Figure 4:
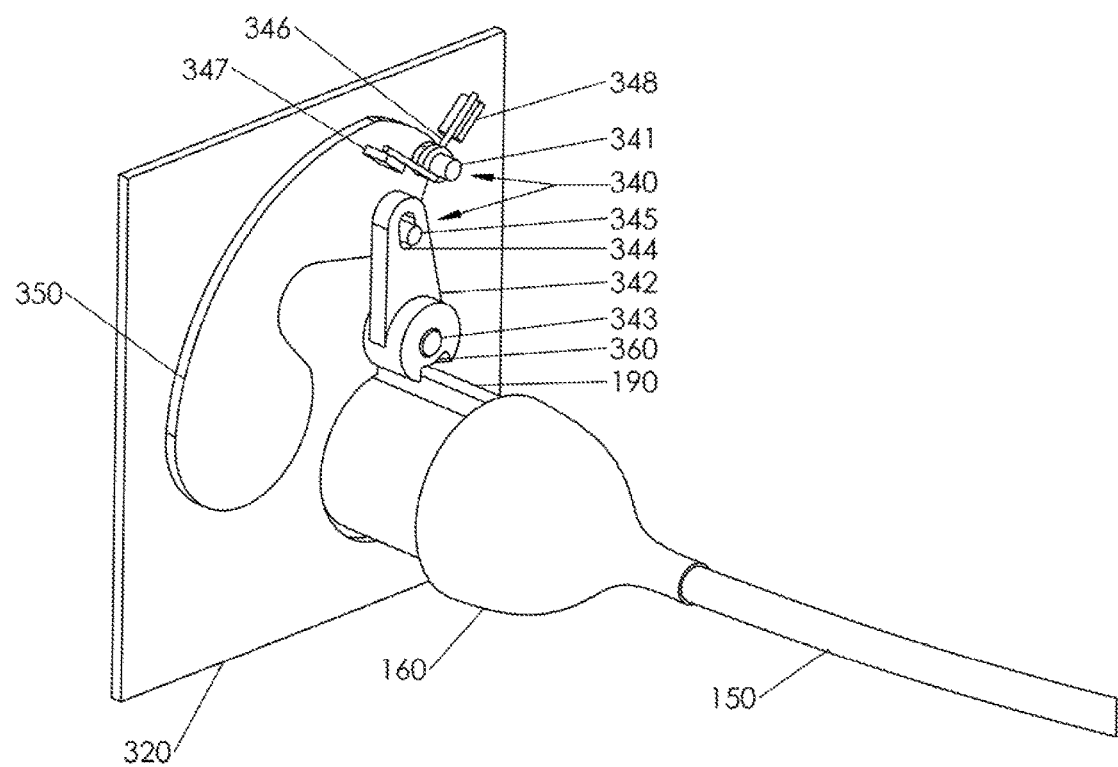
FIG. 4: Close-up view of sensor connector with patient cable connector attached.

Referring to FIG. 4, the activation or actuation of the mechanism 340 occurs when the engagement rib 190 of the patient cable connector 160 slides along the helical-shaped wall surface of the engagement slot 360 of the lever 342. The alignment of the engagement rib 190 is maintained by the keyway 180 (not shown in FIG. 4 as the front panel of the housing has been removed for clarity) of the sensor connector 140, which maintains the orientation of the patient cable connector 160. The rib 190 drives the lever 342 in a counterclockwise direction which, via coupling slot 344 and coupler pivot 345, forces the protective flap 350 to rotate clockwise about flap pivot 341. The rotation of the protective flap 350 to the "open" position allows access to the interconnections, i.e. it allows the optical connections 240 and the electrical connections 250 of the sensor connector 140 to mate with the corresponding interconnections of the patient cable connector 160. This position, where the protective flap 350 has been moved out of the way of the patient cable connector 160 allowing access to the interconnections, is the open position of the protective flap 350. In this open position the two halves of the connector, the patient cable connector 160 and the sensor connector 140, can mate.

The movement of the protective flap 350 is resisted by the torque provided by torsion spring 346 acting on spring stops 347 and 348. This return torque causes the protective flap to return to its normally closed position when the patient cable connector 160 with rib 190 is retracted from the sensor connector. When the protective flap 350 is in the closed position it provides a protective cover for the optical connections of the sensor connector. It protects the delicate optical connections from degradation of optical performance due to contamination from dirt, dust, moisture, and oils or damage from contact with foreign objects such as fingertips and tools. This damage from foreign objects could include the dislodgement or "pushing out" of the end face 230 of the optical light guide from the housing holding the interconnections.

The apparatus shown in FIGS. 3 and 4 is thus a bistable shutter apparatus that moves the protective flap between two preferred positions, an open position that allows access to or reveals the interconnections of the sensor connector and a closed position that protects or blocks access to these interconnections, and specifically the optical connections, from damage or contamination.

By engineering design, in this preferred embodiment, the mechanism uses the mechanical advantage of the design to move the protective flap 350 a large distance with a small angular deflection of the lever 342. The addition of the torsion spring 346 provides a closing torque that moves the protective flap 350 to a position covering the optical connections, the "fail-safe" position, when the patient cable connector 160 is withdrawn or otherwise not present. Thus, regardless of the physical orientation of the electronics module 110, the spring force of the torsion spring 346 returns the protective flap 350 to a closed position when the patient cable connector 160 is withdrawn even if the orientation of the electronics module is such that gravity would naturally be trying to cause the protective flap 350 to fall open.

The protective flap and mechanism illustrated in FIGS. 3 and 4 are one example of a shutter that protects the optical connections of the sensor connector of a photoplethysmographic device with light sources internal to its main electronics module, but countless other mechanical deigns could be envisioned with various combinations of elements including multiple levers, linkages, supports, pivots, stops, fasteners, flaps, and springs that create this apparatus and accomplish the required movements of a protective flap.

The activation and driving of the mechanism 340 could also be accomplished using electrical or magnetic actuators, including small motors, which might remove some mechanical components and complexity. Similarly, the addition of electrically-conductive bands or magnetic elements on the patient cable connector 160 or within the sensor connector 140 could provide the required signal to the monitor that a cable connector is being inserted and that the protective flap should be moved. However, using the insertion force of the user inserting or removing the patient cable connector 160 to actuate the mechanism controlling to protective flap eliminates the need for, and expense associated with, electrical or magnetic components and minimizes the potential for field failures.

One additional feature of the arrangement shown in FIG. 3 is that the projective flap 350 moves in a plane that is essentially parallel to the end face 230 of the optical light guide 220 that forms the optical connection 240. By essentially parallel it is meant that the plane of motion is generally along the end face of the sensor connector and its various interconnections. Moving the protective flap 350 along this plane helps minimize the overall thickness of the sensor connector 140 and the depth that the patient cable connector 160 must be inserted to make contact with the interconnections of the sensor connector.

Figure 5A:
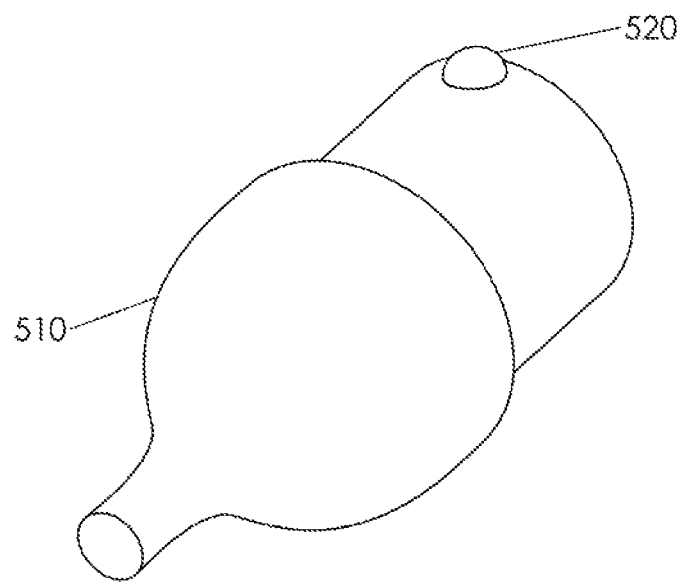
FIG. 5A: Patient cable connector with feature to interact with narrow helical drive slot.
Figure 5B:
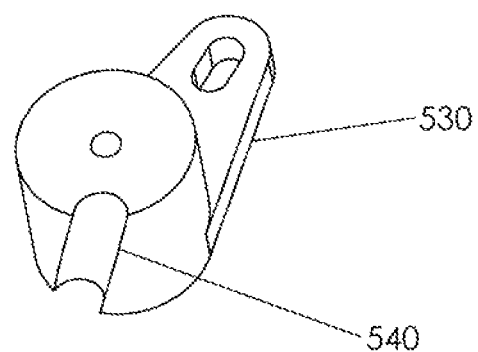
FIG. 5B: Sensor connector mechanism lever with narrow helical drive slot.

A modification of this design can be created by changing the rib 190 on the cable connector 160 and also modifying the engagement slot 360 of lever 342, as shown in FIGS. 5A and 5B. FIG. 5A shows a modified patient cable connector 510 with a small engagement protrusion 520, instead of the engagement rib 190. FIG. 5B shows a modified shutter mechanism lever 530 with narrow helical drive slot 540 that captures the engagement protrusion 520 of the modified connector 510. The modified lever 530 replaces the lever 342 in the shutter mechanism 340 of FIG. 3. In this embodiment, the shutter mechanism and attached protective flap are "driven" to the open position when the modified cable connector 510 is inserted, and similarly are "driven" to the closed position when the cable connector is withdrawn, thereby forcing the protective flap to be in the closed position upon removal of patient cable connector 510 without relying on a spring to provide the return force.

Note also that in the designs of FIGS. 3, 4, and 5, the protective flap 350 fully covers the optical connections just prior to full disengagement, or full exit, of the mating connector (patient cable connector 160 or modified patient cable connector 510) from the front panel of the electronics box 110, thus preventing the insertion of a foreign object that might wedge or hold open the protective flap. Another advantage of these designs is that they achieve a full opening, or closing, of the protective flap with less than 10 mm of insertion, or removal, of the mating connector.

Figure 6:
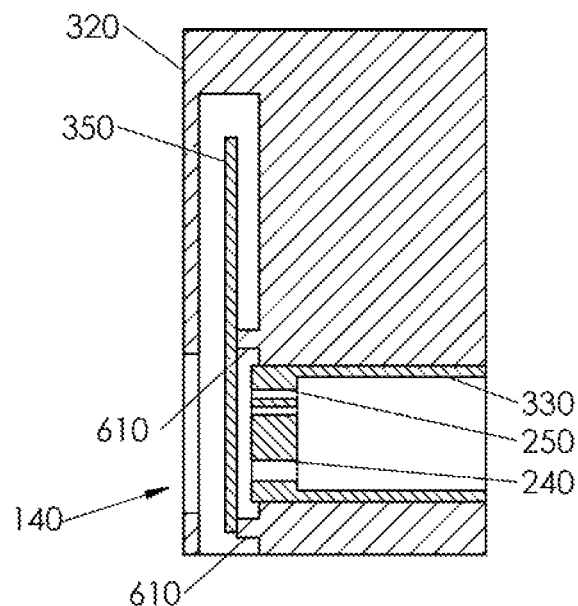
FIG. 6: Protective flap with stand-off supports.

A number of further improvements can be introduced to the protective flap and the structure of the sensor connector to provide additional safeguards from degradation of optical performance due to contamination of the optical connector surfaces or physical damage to the optical or electrical connections of the sensor connector. FIG. 6 shows a cross-section side view of the sensor connector 140 with support posts 610 attached to the housing 320. These posts prevent the protective flap 350 from physically contacting the electrical connections 250 or optical connections 240 disposed within the housing 320 (and further disposed within the connector housing 330) should a fingertip, tool, or other foreign object be pressed against the protective flap in a direction toward the optical connections 240 that are covered by the flap. The physical support provided by the posts 610 is aided by choosing a protective flap material and thickness of sufficient rigidity to withstand a force impressed on the exposed surface. While the force that the protective flap 350 must be able to support without allowing damage to underlying structures is a design choice it should, at a minimum, be sufficient to prevent damage from gently probing fingers. Light finger pressure would be in the range of about 100 grams force or approximately 1 Newton. If the material of the protective flap 350 is absorbing, reflecting, or otherwise blocking or attenuating to optical radiation (i.e. light), the protective flap prevents any unwanted optical radiation emission from exiting an optical interconnection 240 of the sensor connector that could cause injury to either the eyes or skin of a patient or end user. Furthermore, if the material of the protective flap 350 is electrically insulating, the protective flap isolates the patient or end user from any electrical shock hazard that might be present at one or more electrical interconnections 250 of the sensor connector and protects the electrical interconnections 250 from inadvertent electrostatic discharge. There are many choices of suitable materials for the protective flap 350 depending on whether it is desired that the flap be optically attenuating, electrically insulating, or both. A metallic flap provides an effective block for optical radiation and would be stiff enough to prevent physical damage when a force is impressed on or applied to its exposed surface, however it would need to be painted, coated, or covered in a polymer (plastic) layer to also provide electrical insulation. If the protective flap 350 is made from an opaque, non-conducting material such as a polymer or wood, it would be both light blocking and electrically insulating.

Figure 7:
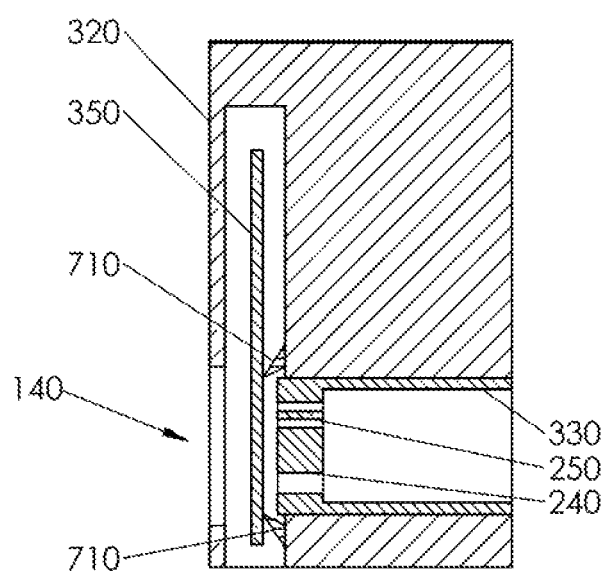
FIG. 7: Protective flap with sealing element.

FIG. 7 shows a cross-section side view of the sensor connector with a sealing element 710 that encircles the connector body 330 portion of the housing 320 and blocks the movement of dirt, dust, moisture, oil, or other contaminants outside the shutter from reaching the optical connections 240. The sealing element could be comprised of a compliant material, such as a rubber or soft polymer, that lightly presses against the protective flap. Alternatively, a compliant element could be added to the protective flap that seals against the entire face of the optical connections.

Figure 8:
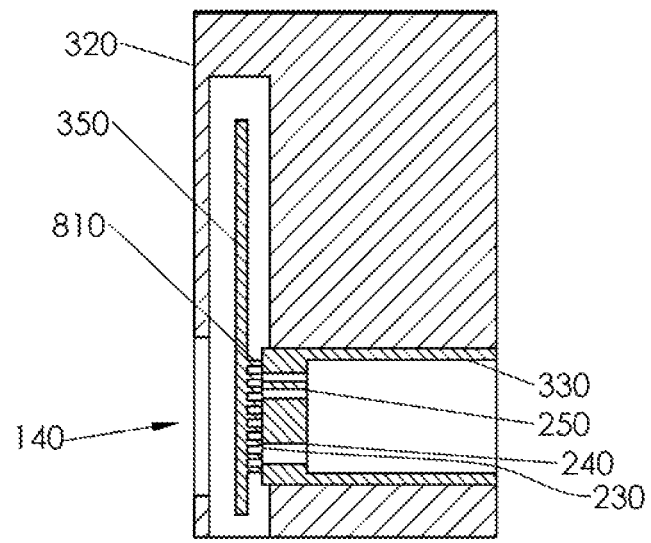
FIG. 8: Protective flap with cleaning element.

FIG. 8 shows a cross-section side view of the sensor connector with a cleaning element 810 disposed onto the face of the protective flap 350. The cleaning element might be a series of brush-like features, a compliant fabric pad, or other soft material mounted on, or otherwise integral to, the protective flap. This cleaning element might also be a replaceable element so that a new cleaning surface could be installed periodically, or otherwise cleaned, thus replacing, removing, or cleaning a cleaning element that has become soiled. The cleaning element works by employing a mechanism similar to that shown in FIG. 3, wherein the protective flap moves in a plane essentially parallel to the face of the interconnections, so that the cleaning element "wipes" the protective flap across the end face 230 of the optical light guide, causing a cleaning action on the optical connection 240, thereby removing dirt, dust, oils, or other contaminants.

Figure 9:
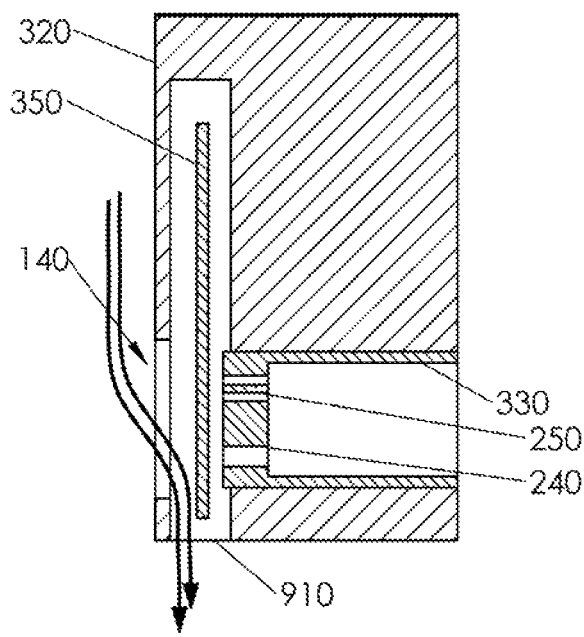
FIG. 9: Water-shedding sensor connector.

By design choice, the shape and arrangement of the protective flap 350 could also provide a liquid-shedding feature to the design, as shown in FIG. 9. The protective flap in the closed position overlaps the extents of the interconnections 240 and 250, and any liquid (indicated in FIG. 9 by the two parallel dark arrows) that flows into the patient cable connector hole of the front panel sensor connector 140 of the electronics module 110 flows over the protective flap 350 and misses the interconnections. This liquid-shedding feature is further improved if the protective flap 350 is disposed within the monitor as shown in FIG. 9 and the patient cable connector 160 reaches any interconnections through an access hole that has a smaller area than that of the protective flap. This liquid-shedding feature could also be aided by adding a drain or vent 910 in the bottom of the housing 320 to channel away any liquid that enters the access hole and is shed by the protective flap.

The previous discussion of the embodiments has been presented for the purposes of illustration and description. The description is not intended to limit the invention to the form disclosed herein. Variations and modifications commensurate with the claims are considered to be within the scope of the present invention. The embodiments described herein are further intended to explain the best modes presently known of practicing the invention and to enable others skilled in the art to utilize the invention as such, or in other embodiments, and with the particular modifications required by their particular application or uses of the invention. It is intended that the appended claims be construed to include alternative embodiments to the extent permitted by the prior art.

The invention claimed is:

1. A photoplethysmographic device for use with a patient cable connector, the photoplethysmographic device comprising:
   a) an electronics module configured to process photoplethysmographic signals to measure and output at least one or more blood analyte levels or one or more physiological parameters;
   b) the electronics module including a plurality of light sources;
   c) at least one of the plurality of light sources being a laser;
   d) at least one of the lasers coupled to an optical light guide that terminates in an optical connection, the optical connection having an end face;
   e) the electronics module further including a sensor connector comprising a plurality of interconnections, a protective flap, and a mechanism, the plurality of interconnections, the protective flap, and the mechanism disposed within a housing;
   f) at least one of the plurality of interconnections is the optical connection;
   g) the mechanism in communication with the protective flap;
   h) the mechanism configured to control movement of the protective flap;
   i) movement of the protective flap providing at least a substantially open position and a substantially closed position;
   j) the protective flap when oriented in the substantially closed position covering at least one of the optical connections;
   k) the mechanism actuated by insertion or removal of the patient cable connector; and
   l) the protective flap in the substantially closed position designed to prevent degradation of at least one of the optical connections when a force of less than or equal to 0.25 Newtons is applied to the protective flap in a direction toward the at least one optical connection covered by the protective flap.

2. The apparatus of claim 1 wherein the optical light guide has a core and cladding diameter of less than 300 um.

3. The apparatus of claim 1 wherein the protective flap is electrically insulating.

4. The apparatus of claim 1 wherein the sensor connector is water shedding when the protective flap is in the substantially closed position.

5. The apparatus of claim 1 wherein the protective flap is mechanically forced to the substantially open position by insertion of the patient cable connector and the protective flap is mechanically forced to the substantially closed position by removal of the patient cable connector.

6. The apparatus of claim 1 wherein the protective flap is configured to move to the substantially open position with less than 10 mm of insertion of the patient cable connector.

7. The apparatus of claim 1 wherein the protective flap incorporates a sealing element.

8. The apparatus of claim 1 wherein the protective flap moves along a plane that is substantially parallel to the end face of the optical connection.

9. The apparatus of claim 8 wherein the protective flap incorporates a cleaning element that wipes the end face of the optical connection upon movement of the protective flap.

10. The apparatus of claim 1 wherein the protective flap is moved to the substantially closed position prior to the patient cable connector fully exiting the housing whereby access is prevented to the one or more optical connections covered by the protective flap when the protective flap is in the substantially closed position.

11. A method of manufacturing a photoplethysmographic device for use with a patient cable connector including the steps of:
  a) providing an electronics module;
  b) configuring the electronics module to process photoplethysmographic signals to measure and output at least one or more blood analyte levels or one or more physiological parameters;
  c) providing at least one laser within the electronics module;
  d) coupling the laser to an optical light guide and terminating the optical light guide in an optical connection, the optical connection having an end face;
  e) providing a sensor connector comprising a plurality of interconnections, a protective flap, and a mechanism, the plurality of interconnections, the protective flap, and the mechanism disposed within a housing included in the electronics module;
  f) positioning at least one of the optical connections as at least one of the plurality of interconnections;
  g) designing the mechanism to control movement of the protective flap to provide bistable positioning of the protective flap in either a substantially open position or a substantially closed position;
  h) positioning at least one of the optical connections within the housing to be covered by the protective flap when the protective flap is oriented in the substantially closed position;
  i) designing the mechanism to be actuated by insertion or removal of the patient cable connector with insertion of the patient cable connector causing the protective flap to move to a substantially open position and removal of the patient cable connector causing the protective flap to move to a substantially closed position; and
  j) designing the protective flap to prevent degradation to the covered optical connection when a force of at least 0.25 Newtons is applied to the protective flap in a direction toward the at least one optical connection covered by the protective flap when the protective flap is in the substantially closed position.

12. The method of claim 11 further including the step of designing the sensor connector to shed water away from the covered interconnections including the at least one optical connection when the protective flap is in the substantially closed position.

13. The method of claim 11 further including the step of designing the mechanism to move the protective flap to a substantially open position after less than 10 mm of insertion of the patient cable connector.

14. The method of claim 11 further including the step of disposing a sealing element onto the protective flap.

15. The method of claim 11 further including the step of designing the mechanism to move the protective flap along a plane that is substantially parallel to the end face of the optical connection.

16. The method of claim 15 further including the step of disposing a cleaning element onto the protective flap that wipes the end face of the optical connection upon movement of the protective flap.

17. The method of claim 11 further including the step of designing the mechanism controlling the movement of the protective flap to cause the protective flap to be moved to the substantially closed position prior to the patient cable connector fully exiting the housing whereby access is prevented to the one or more optical connections covered by the protective flap when the protective flap is in the substantially closed position.

18. A photoplethysmographic device for use with a patient cable connector, the photoplethysmographic device comprising:
  a) an electronics module configured to process photoplethysmographic signals to measure and output at least one or more blood analyte levels or one or more physiological parameters;
  b) the electronics module including a plurality of laser light sources;
  c) at least one laser light source coupled to at least one optical light guide that terminates in an optical connection;
  d) the optical light guide having a core and cladding diameter of less than 300 um;
  e) the electronics module further including a sensor connector comprising a plurality of interconnections, a protective flap, and a mechanism, the plurality of interconnections, the protective flap, and the mechanism disposed within a housing;
  f) the mechanism in communication with the protective flap;
  g) the mechanism configured to control movement of the protective flap;
  h) movement of the protective flap providing a substantially closed position that covers the plurality of interconnections, the plurality of interconnections comprising at least one of the optical connections and at least one electrical connection, and a substantially open position that reveals said plurality of interconnections;
  i) the mechanism for controlling the position of the protective flap designed to mechanically force the protective flap to the substantially open position by less than 10 mm of insertion of the patient cable connector, and
  j) the mechanism for controlling the position of the protective flap designed to hold the protective flap in the substantially closed position when no patient cable connector is inserted.

* * * * *